July 31, 1973 S. COUTRAKIS Plant Pat. 3,384
AZALEA PLANT
Filed April 24, 1972
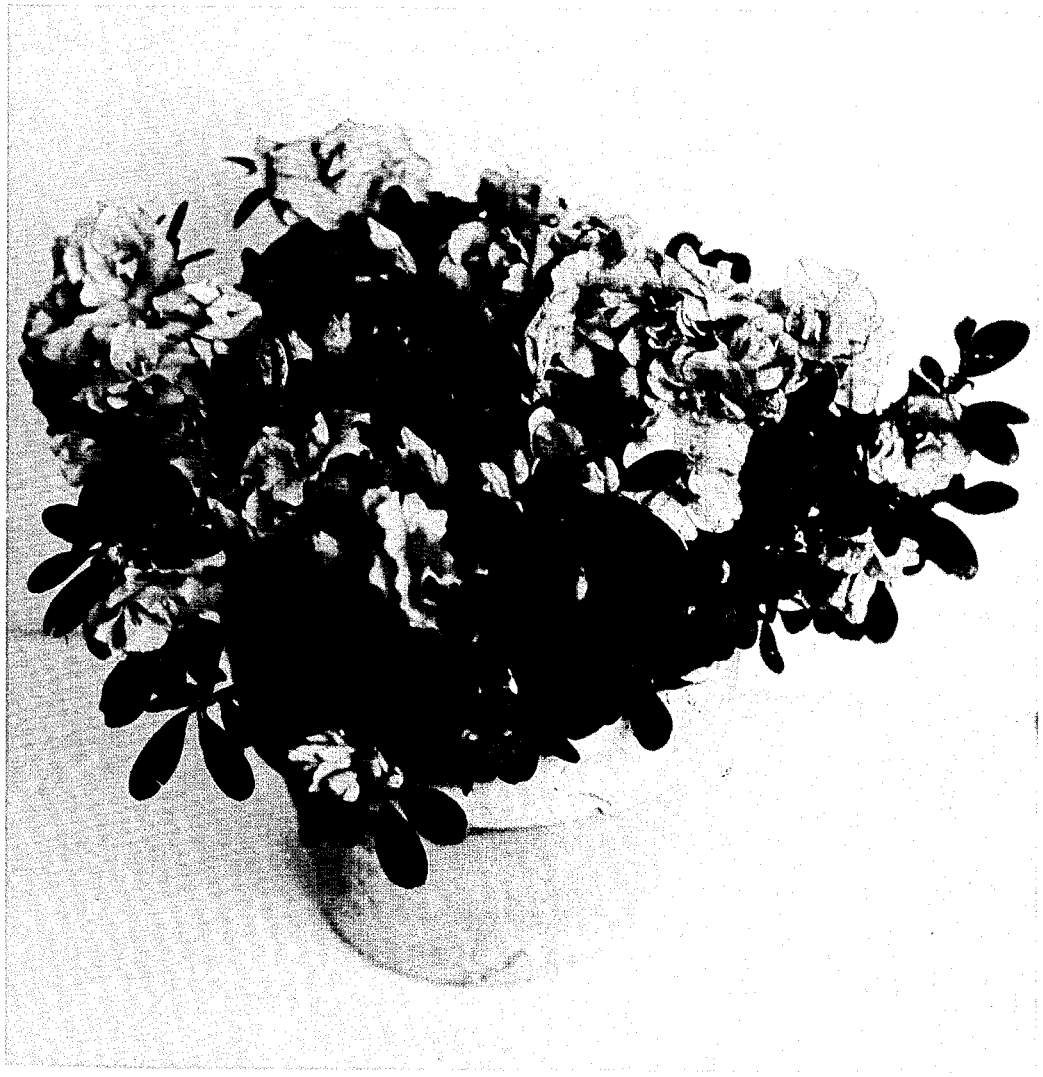

United States Patent Office

Plant Pat. 3,384
Patented July 31, 1973

3,384

AZALEA PLANT

Steve Coutrakis, 929 W. Main St.,
Ripon, Calif. 95366

Filed Apr. 24, 1972, Ser. No. 247,194
Int. Cl. A01h 5/00
U.S. Cl. Plt.—56 1 Claim

ABSTRACT OF THE DISCLOSURE

An azalea plant—of the Belgian Indica class, and of greenhouse forcing and garden type readily reproduced by cuttings—which is dense, bushy, well branched but symmetrical, and foliated with oval, heavy textured, glossy but very slightly pubescent, medium size leaves of medium green color on the top side, and lighter green on the under side; the plant blooming profusely and substantially evenly over the entire plant, with large, persistent, hose in hose, with some double, bright pink flowers having velvety petals slightly ruffled at the edges, and the flowers being borne in clusters of two to eight held relatively high above the foliage by strong medium length stems.

BACKGROUND OF THE VARIETY

I am engaged in the commercial growing of azalea plants for florist and garden use, and, in the pursuance of such line of endeavor, there is produced—by cross-breeding—new and improved varieties of such plants. The present variety of azalea plant resulted from such activity.

ORIGIN OF THE VARIETY

The present variety of azalea plant was originated, in my nursery located in Ripon, San Joaquin County, Calif., as a cross between a seedling of Violacea and Chimes; the Violacea being the pollen parent, and both of such parent varieties being unpatented. Subsequent to origination of the present variety of azalea plant, it was recognized as having certain new and distinctive characteristics which were indicative of excellence for commercial growing, and, therefore, the variety was selected for asexual reproduction.

ASEXUAL REPRODUCTION OF THE VARIETY

By cuttings from the original plant, I have reproduced, in my nursery located as aforesaid, the present variety of azalea plant, and—when grown to maturity—such reproductions were found to carry forward all of the characteristics of said original plant, and, hence, are fixed in the floricultural characteristics thereof.

SUMMARY OF THE VARIETY

The present variety of azalea plant is of Belgian Indica class, is of greenhouse forcing and garden type readily reproduced from cuttings, and is dense, bushy, well branched but symmetrical, and foliated with oval, heavy textured, glossy but very slightly pubescent, medium size leaves of medium green color on the top side, and lighter green on the under side; the plant blooming profusely and substantially evenly over the entire plant, with large, persistent, hose in hose, with some double, bright pink flowers having velvety petals slightly ruffled at the edges, and the flowers being borne in clusters of two to eight held relatively high above the foliage by strong medium length stems.

Further, the present variety of azalea plant is characterized—in comparison to the Jeans Hearrens azalea (unpatented)—by general resemblance of the plant, by faster and more compact plant growth, and by flowers of generally the same size but of a ligheter pink color.

BRIEF DESCRIPTION OF THE DRAWING

The drawing is an illustration, by photographic reproduction in color, showing a plant, in bloom, of the variety.

DESCRIPTION OF THE VARIETY

The fluoricultural details of this new and distinct variety of azalea plant—with color definitions (except those in common color terms) referenced to Maerz and Paul Dictionary of Color—are as follows:

Plant:

*Form.*—Well branched, symmetrical, height and breadth substantially equal in young plants, with breadth gradually becoming relatively greater with continued growth.

*Growing habit.*—Dense, bushy, grows to 2" to 2½" spread in four growing seasons from cuttings.

*Blooming habit.*—Profuse, flowers substantially evenly over entire plant, 1 to 8 (or more) flowers on each stem.

*Blooming season.*—March 20th to April 20th, but readily forces into bloom out of season in greenhouse.

Foliage:

*Size.*—Medium, average length—1" to 2½", average with—½" to 2".

*Color.*—Top side—medium green (24–L–9), under side—lighter green (21–J–6).

*Shape.*—Oval.

*Aspect.*—Glossy, but with very slight pubescence.

*Texture.*—Heavy.

*Edge.*—Smooth.

*Ribs and veins.*—Normal.

*Disease resistance.*—No unusual susceptibilities observed.

Flower:

*Floret.*—Size—large, average 2½" to 4½" in diameter. Borne—clusters of 2 to 8 held relatively high above foliage on strong medium length stems. Form—hose in hose, with some double. Permanace—long lasting. Petalage—5 petals on each hose or trumpet. Color—Bright pink (2–H–5).

*Petals.*—Texture—heavy. Appearance — velvety—both sides. Edges—slightly ruffled. Size—average length—1½" to 2", average width—1¼" to 1½". Shape—ovate, narrowing at lower end. Arrangement—normal. Persistence—remain firm, without wilting, until flowers ready to fall.

*Reproductive organs.*—Stamens—average—5 or 6, somewhat deeper in color than petals. Pollen—white, anthers similar in color to stamens. Style—style and stigma well developed and similar in color to the stamens. Ovaries—normal.

The azalea plant and its flower herein described may vary in slight detail due to climatic and soil conditions under which the variety may be grown; the present description being of the variety as grown in the Central Valley of California.

I claim:

1. A new and distinct variety of azalea plant of the Belgian Indica class, substantially as illustrated and described, which is dense, bushy, well branched but symmetrical, and foliated with oval, heavy textured, glossy but very slightly pubescent, medium size leaves of medium green color on the top side and lighter green on the under side; the plant blooming profusely and substantially evenly over the entire plant, with large, persistent, hose in hose, with some double, bright pink flowers having velvety petals slightly ruffled at the edges, and the flowers being borne in clusters of two to eight held relatively high above the foliage by strong medium length stems; the variety, in comparison to the Jeans Hearrens, being further characterized by general resemblance of the plant, by faster and more compact plant growth, and by flowers of generally the same size but of a lighter pink color.

No references cited.

ROBERT E. BAGWILL, Primary Examiner